United States Patent
Chen et al.

(10) Patent No.: US 11,848,075 B2
(45) Date of Patent: Dec. 19, 2023

(54) BIOMARKER DETECTION METHOD, DISEASE ASSESSMENT METHOD, BIOMARKER DETECTION DEVICE, AND COMPUTER READABLE MEDIUM

(71) Applicant: JAPAN SCIENCE AND TECHNOLOGY AGENCY, Saitama (JP)

(72) Inventors: Luonan Chen, Tokyo (JP); Kazuyuki Aihara, Tokyo (JP); Xiaoping Liu, Tokyo (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 691 days.

(21) Appl. No.: 16/612,276

(22) PCT Filed: May 11, 2018

(86) PCT No.: PCT/JP2018/018393
§ 371 (c)(1),
(2) Date: Nov. 8, 2019

(87) PCT Pub. No.: WO2018/207925
PCT Pub. Date: Nov. 15, 2018

(65) Prior Publication Data
US 2021/0158899 A1    May 27, 2021

(30) Foreign Application Priority Data

May 12, 2017 (JP) ................................ 2017-096060

(51) Int. Cl.
*G16B 50/30*    (2019.01)
*G01N 33/574*   (2006.01)
(Continued)

(52) U.S. Cl.
CPC ............ *G16B 40/00* (2019.02); *A61B 5/7246* (2013.01); *G01N 33/57484* (2013.01);
(Continued)

(58) Field of Classification Search
CPC ........... G01N 33/689; G01N 2800/368; G01N 2800/60; G01N 33/57484; G01N 33/49;
(Continued)

(56) References Cited

U.S. PATENT DOCUMENTS

2005/0142573 A1    6/2005  Glinskii
2011/0224101 A1*   9/2011  Ling ...................... C40B 40/04
                                                         250/282
(Continued)

FOREIGN PATENT DOCUMENTS

CN    105009130        10/2015
JP    2005323573 A     11/2005
(Continued)

OTHER PUBLICATIONS

Yang et al., Systematic computation with functional gene-sets among leukemic and hematopoietic stem cells reveals a favorable prognostic signature for acute myeloid leukemia, Mar. 24, 2015 [retrieved Jun. 18, 2022], BMC Bioinformatics, vol. 16, Article: 97 (2015), 21 pages. Retrieved: (Year: 2015).*

(Continued)

*Primary Examiner* — Matthew C Bella
*Assistant Examiner* — Dennis Rosario
(74) *Attorney, Agent, or Firm* — Fox Rothschild LLP; Carol Thorstad-Forsyth

(57) ABSTRACT

Provided is a method for detecting a biomarker indicating states of a target biological system based on data acquired by measuring the target biological system. The method includes the steps of: preparing a reference dataset based on data acquired from one or more reference biological systems;

(Continued)

generating a target dataset by adding, to the reference dataset, target biological data acquired from the target biological system; acquiring first correlation coefficients between a plurality of factor items in the reference dataset; acquiring second correlation coefficients between the plurality of factor items in the target dataset; acquiring difference correlation coefficients that are differences between the first correlation coefficients and the second correlation coefficients; acquiring indexes respectively for the plurality of factor items based on the difference correlation coefficients; and selecting the biomarker based on the indexes.

12 Claims, 9 Drawing Sheets

(51) Int. Cl.
  *A61B 5/00* (2006.01)
  *G16B 40/00* (2019.01)
  *G16B 30/10* (2019.01)
  *G06T 7/00* (2017.01)

(52) U.S. Cl.
  CPC ............. *G16B 30/10* (2019.02); *G16B 50/30* (2019.02); *G01N 2800/60* (2013.01); *G06T 7/0012* (2013.01); *G06T 2207/30004* (2013.01)

(58) Field of Classification Search
  CPC ............. G01N 33/491; G01N 33/6893; G01N 2800/56; G01N 2333/4745; G01N 2333/475; G01N 2800/50; G01N 2333/65; C12Q 2600/158; C12Q 1/6883; C12Q 2600/156; C12Q 1/6886; C12Q 2600/106; C12Q 2600/154; G16B 40/00; G16B 20/00; G16B 20/20; G16B 20/40; G16B 40/20; G16B 40/30; G16B 40/10; G16H 50/20; G16H 10/40; G16H 50/30; G06T 2207/30104; G06T 7/0012; G06T 2207/30004; C12N 2502/11; A61B 5/7275; A61B 5/7246; C07K 16/22
  See application file for complete search history.

(56) References Cited

U.S. PATENT DOCUMENTS

| | | | | |
|---|---|---|---|---|
| 2014/0236621 | A1* | 8/2014 | Six | G16H 50/50 705/2 |
| 2015/0278433 | A1* | 10/2015 | Aihara | G16B 30/00 702/19 |
| 2015/0302165 | A1 | 10/2015 | Aihara et al. | |
| 2017/0108502 | A1* | 4/2017 | Mulvihill | G01N 33/57488 |

FOREIGN PATENT DOCUMENTS

| | | |
|---|---|---|
| JP | 2014064515 A | 4/2014 |
| WO | 2014050160 A1 | 4/2014 |

OTHER PUBLICATIONS

[item U continued] https://link.springer.com/article/10.1186/s12859-015-0510-7 (Year: 2015).*
Liu et al., Quantifying critical states of complex diseases using single-sample dynamic network biomarkers, Jul. 5, 2017 [retrieved Nov. 2, 2022], PLOS Computational Biology, 21 pages. Retrieved: https://journals.plos.org/ploscompbiol/article?id=10.1371/journal.pcbi.1005633 (Year: 2017).*
Lena et al., Optimal global alignment of signals by maximization of Pearson correlation, May 27, 2010:online [retrieved Nov. 2, 2022], Information Processing Letters, vol. 110, Issue 16, pp. 679-686. Retrieved: https://www.sciencedirect.com/science/article/pii/S002001901000147X (Year: 2010).*
Tusher et al., Significance analysis of microarrays applied to the ionizing radiation response, Apr. 17, 2001 [retrieved Nov. 3, 2022], PNAS, vol. 98, No. 9, pp. 5116-5121. Retrieved: https://www.pnas.org/doi/abs/10.1073/pnas.091062498 (Year: 2001).*
Yu et al., Individual-specific edge-network analysis for disease prediction, Sep. 13, 2017 [retrieved Mar. 14, 2023], Nucleic Acids Research, vol. 45, No. 20, 11 pages. Retrieved: https://academic.oup.com/nar/article/45/20/e170/4128862 (Year: 2017).*
Liu et al., Personalized characterization of diseases using sample-specific networks, Sep. 4, 2016 [retrieved Mar. 14, 2023], Nucleic Acids Research, vol. 44, No. 22, 18 pages. Retrieved: https://academic.oup.com/nar/article/44/22/e164/2691334#google_vignette (Year: 2016).*
Vafaee, Using Multi-objective Optimization to Identify Dynamical Network Biomarkers as Early-warning Signals of Complex Diseases, Feb. 24, 2016 [retrieved Mar. 14, 2023], Scientific Reports, vol. 6, Article No. 22023 (2016), pp. 1-12. Retrieved: https://www.nature.com/articles/srep22023 (Year: 2016).*
Liu, et al.: "Pituitary Apoplexy," Seminars in Neurosurgery 12, Thieme, pp. 315-320 (2001).
Paek SH et al. "Hearing preservation after gamma knife stereotactic radiosurgery of vestibular schwannoma," Cancer 104, Wiley-Blackwell, pp. 580-590 (2005).
Jose G. Venegas et al.: "Self-organized patchiness in asthma as a prelude to catastrophic shifts," Nature 434, Nature Publishing Group, pp. 777-782 (2005).
Patrick E. McSharry, et al.: "Prediction of epileptic seizures: are nonlinear methods relevant?," Nature Medicine 9, Nature Publishing Group, pp. 241-242 (2003).
Roberto Pastor-Barriuso, et al.: "Transition models for change-point estimation in logistic regression," Statistics in Medicine 22(7), Wiley-Blackwell, pp. 1141-1162 (2003).
First Office Action issued by CNIPA in Chinese Patent Application No. 201880028570.8, 12 pages (dated Mar. 31, 2023).

* cited by examiner

FIG. 4
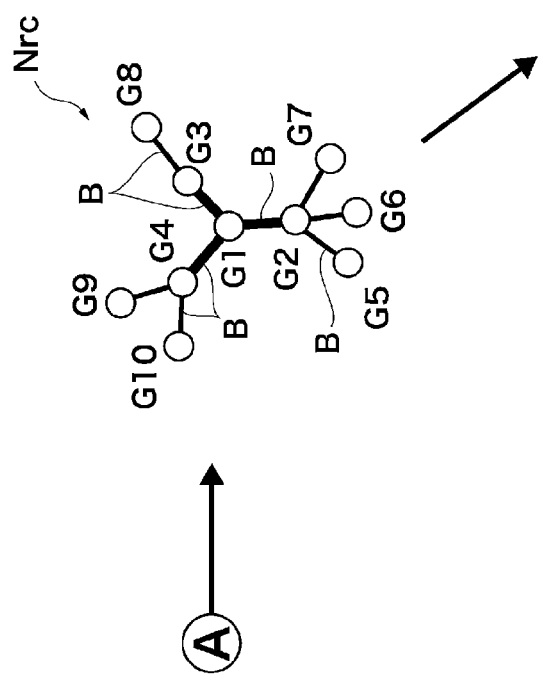
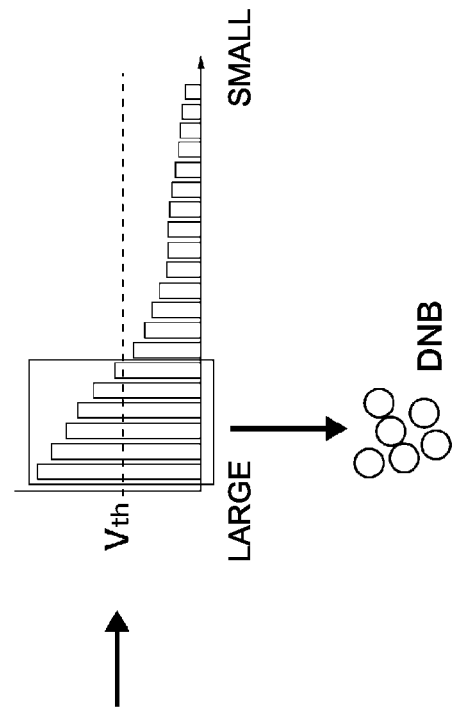

BIOMARKER DETECTION METHOD, DISEASE ASSESSMENT METHOD, BIOMARKER DETECTION DEVICE, AND COMPUTER READABLE MEDIUM

CROSS REFERENCE TO RELATED APPLICATIONS

The present application is a U.S. National Phase of International Patent Application No. JP/2018/018393, filed on May 11, 2018 and entitled "BIOMARKER DETECTION METHOD, DISEASE ASSESSMENT METHOD, BIOMARKER DETECTION DEVICE, AND BIOMARKER DETECTION PROGRAM," which claims priority to Japanese Patent Application No. 2017-096060, filed on May 12, 2017, the contents of which are incorporated herein by reference in their entireties.

TECHNICAL FIELD

The present invention relates to a biomarker detection method, a disease assessment method, a biomarker detection device, and a computer readable medium for detecting a biomarker indicating a state of a biological system, based on data of factor items acquired by measuring the biological system.

BACKGROUND ART

The states of a biological system (such as health state) are known to change drastically to a disease state from a good or normal (hereinafter referred to simply as "good") state after passing a certain critical point (tipping point) as in a complex system such as a weather system, an ecological system, or an economic system (see Patent Literature 1 and Non-Patent Literatures 1 to 5). In the complex system, it is known that its parameters fluctuate increasingly at the critical point and there exist some parameters whose fluctuations are strongly correlated. One of the reasons for this is that the resilience to maintain the system stable is reduced, so that the system is made vulnerable to disturbance.

An example of a case where a person is getting a disease will be described below with reference to FIG. 1. FIG. 1 is a schematic view illustrating a process of disease progression. In FIG. 1, a vertical axis conceptually represents the health state, indicating that the health state gets deteriorated toward an opposite direction to an arrow (downward direction). A horizontal axis represents time. Point "a" in FIG. 1 indicates that a person is in good health. In this point, the person notices no symptoms at all and gets no specific abnormal results of a conventional medical examination. As shown in FIG. 1, even though the health state is deteriorated as time passes, the change is extremely gradual, so that the person still does not feel any change in physical condition. However, if the health state is gradually getting worse, thereby reaching a critical state denoted by point "b" in FIG. 1 (between a normal state and a disease state), the health state gets deteriorated drastically (or gradually in some cases) and comes to an early-disease state (point "c"). Upon reaching such state, the person comes to feel ill and lapses into a disease state (point "d") after a while. The critical state (point b) herein is a state where the person does not notice any specific symptoms but there is a high possibility of developing into an early-disease state in no time.

CITATION LIST

Patent Literature

Patent Literature 1: International Publication No. WO2014/050160

Non-Patent Literature

Non-Patent Literature 1: Jose G. Venegas, Tilo Winkler, Guido Musch, Marcos F. Vidal Melo, Dominick Layfield, Nora Tgavalekos, Alan J. Fischman, Ronald J. Callahan, Giacomo Bellani, and R. Scott Harris, "Self-organized patchiness in asthma as a prelude to catastrophic shifts," Nature 434, Nature Publishing Group, pp. 777-782 (2005)

Non-Patent Literature 2: Patrick E. McSharry, Leonard A. Smith, and Lionel Tarassenko, "Prediction of epileptic seizures: are nonlinear methods relevant?," Nature Medicine 9, Nature Publishing Group, pp. 241-242 (2003)

Non-Patent Literature 3: Roberto Pastor-Barriuso, Eliseo Guallar, and Josef Coresh, "Transition models for change-point estimation in logistic regression," Statistics in Medicine 22(7), Wiley-Blackwell, pp. 1141-1162 (2003)

Non-Patent Literature 4: Paek S H et al. "Hearing preservation after gamma knife stereotactic radiosurgery of vestibular schwannoma," Cancer 104, Wiley-Blackwell, pp. 580-590 (2005)

Non-Patent Literature 5: Liu, J. K., Rovit, R. L., and Couldwell, W. T., "Pituitary Apoplexy," Seminars in Neurosurgery 12, Thieme, pp. 315-320 (2001)

SUMMARY OF INVENTION

Technical Problem

People usually go to see a doctor when they feel ill, that is, after passing the critical state (point b) and reaching an early-disease state (point c) or a disease state (point d). In hospitals, medical examinations, diagnostic imaging tests, and other tests are conducted. In such a diagnosis, in most cases, when an abnormality is found in the medical examination and the diagnostic imaging tests, the person who got the diagnosis has already suffered from a disease.

On the other hand, if the above-mentioned critical state (point b) can be detected (early detection), treatment at this point (early treatment) can prevent reaching an early disease state (point c) (in other words, it is not necessary to get sick) and it is estimated that a good health state (point a) can be maintained.

In view of the foregoing, the present invention provides a biomarker detection method, a disease assessment method, a biomarker detection device, and a computer readable medium for detecting a critical state (between a normal state and a disease state) before transitioning to the disease state.

A first aspect of the present invention provides a method for detecting a biomarker indicating a critical state before transitioning to a disease state of a target biological system (Se) based on data acquired by measuring the target biological system. The method includes the steps of: preparing a reference dataset (Dr) based on data acquired from one or more reference biological systems ($S_1, S_2, \ldots,$ and/or $S_n$));

generating a target dataset (Dc) by adding, to the reference dataset (Dr), target biological data acquired from a target biological system (Se); acquiring first correlation coefficients (PCCr) between a plurality of factor items (e.g., $g_1$, $g_2$) in the reference dataset; acquiring second correlation coefficients (PCCc) between the plurality of factor items (e.g., $g_1$, $g_2$) in the target dataset; acquiring difference correlation coefficients (ΔPCC=PCCr−PCCc) that are differences between the first correlation coefficients (PCCr) and the second correlation coefficients (PCCc); acquiring a first average value (sPCCin) of the difference correlation coefficients (ΔPCC) between one factor item (e.g., $g_1$) in the target biological data and a first one or more factor items (e.g., $g_2$, $g_3$, $g_4$) having a prescribed correlation coefficient with respect to the one factor item, among the plurality of factor items; acquiring a second average value (sPCCout) of the difference correlation coefficients (ΔPCC) between the first one or more factor items (e.g., $g_2$) and a second one or more factor items (e.g., $g_5$, $g_6$, $g_7$, $g_8$, $g_9$, $g_{10}$) having a prescribed correlation coefficient with respect to the first one or more factor items, among the plurality of factor items (where the second one or more factor items does not comprise the one factor item); acquiring an average value of a plurality of data items for the one factor item among the plurality of factor items in the reference dataset; acquiring a difference (sED) between the average value and data of the one factor item in the target biological data; acquiring an index (Is) by an equation given by (the difference×the first average value)/(the second average value) (e.g., Is=(sED× sPCCin)/sPCCout); and detecting the biomarker indicating the critical state before transitioning to the disease state of the target biological system based on the indexes (Is).

A second aspect of the present invention provides a biomarker detection device for detecting a biomarker as indexes of states of a target biological system as an examination target based on data of a plurality of factor items acquired by measuring the target biological system. The biomarker detection device includes: a first memory configured to store a reference dataset based on data of a plurality of factor items in reference biological data acquired from one or more reference biological systems; a second memory configured to store a target dataset generated by adding, to the reference dataset, the data of the plurality of factor items in a target biological data acquired from the target biological system; and a control unit configured to: acquire first correlation coefficients between the plurality of factor items in the reference dataset stored in the first memory; acquire second correlation coefficients between the plurality of factor items in the target dataset stored in the second memory; acquire difference correlation coefficients that are differences between the first correlation coefficients and the second correlation coefficients; acquire the indexes respectively for the plurality of factor items based on the difference correlation coefficients; and select the biomarker based on the indexes.

A third aspect of the present invention provides a non-transitory computer readable medium having instructions stored thereon for detecting a biomarker. The instructions cause a computing device to perform the method described above.

Advantageous Effects of Invention

According to some embodiments of the present invention, the following effects can be acquired: (1) an index (new biomarker) indicating a critical state before transiting to a disease state can be specified; and (2) an early diagnosis is possible by using the index.

BRIEF DESCRIPTION OF DRAWINGS

FIG. 4 is a schematic view continued from FIG. 3 illustrating the biomarker detection method according to the first embodiment of the present invention.

DESCRIPTION OF EMBODIMENTS

Exemplary embodiments of the present invention will be described below with reference to the accompanying drawings. The same or similar reference signs are used to designate the same or similar members or elements throughout the drawings, and duplicated explanations are omitted.

First Embodiment

Figure 2:
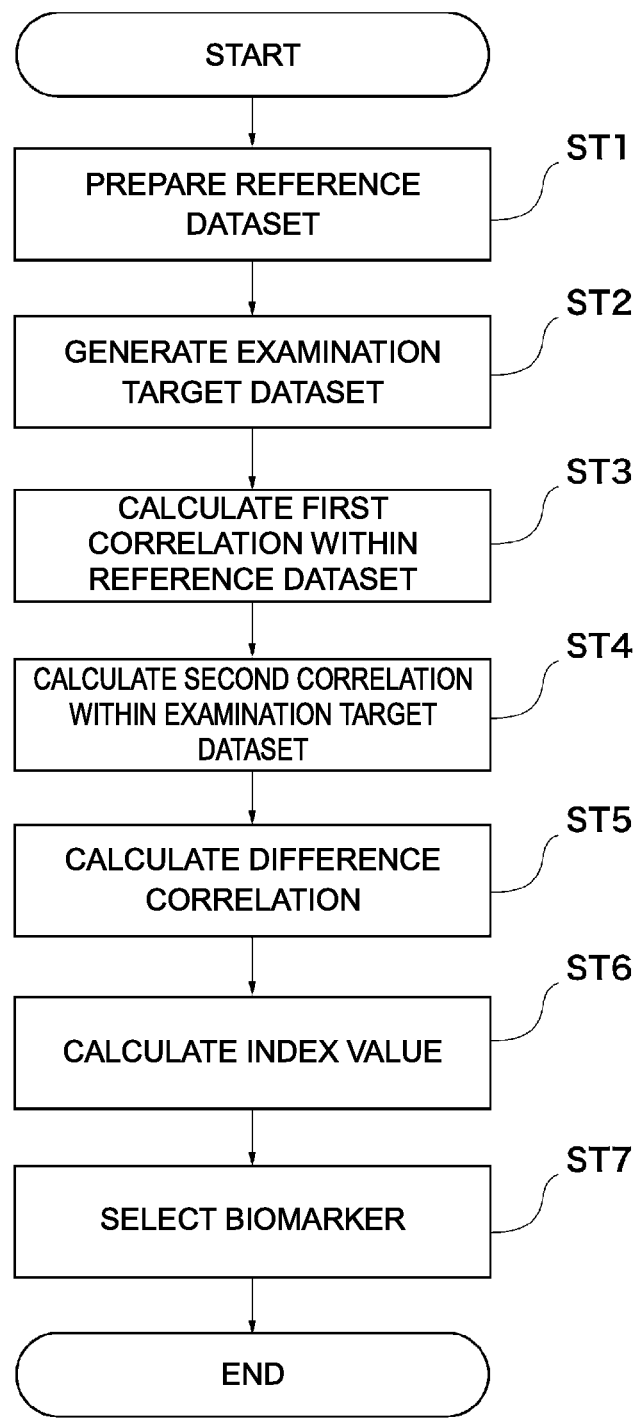
FIG. 2 is a flowchart illustrating a biomarker detection method according to a first embodiment of the present invention.
Figure 3:
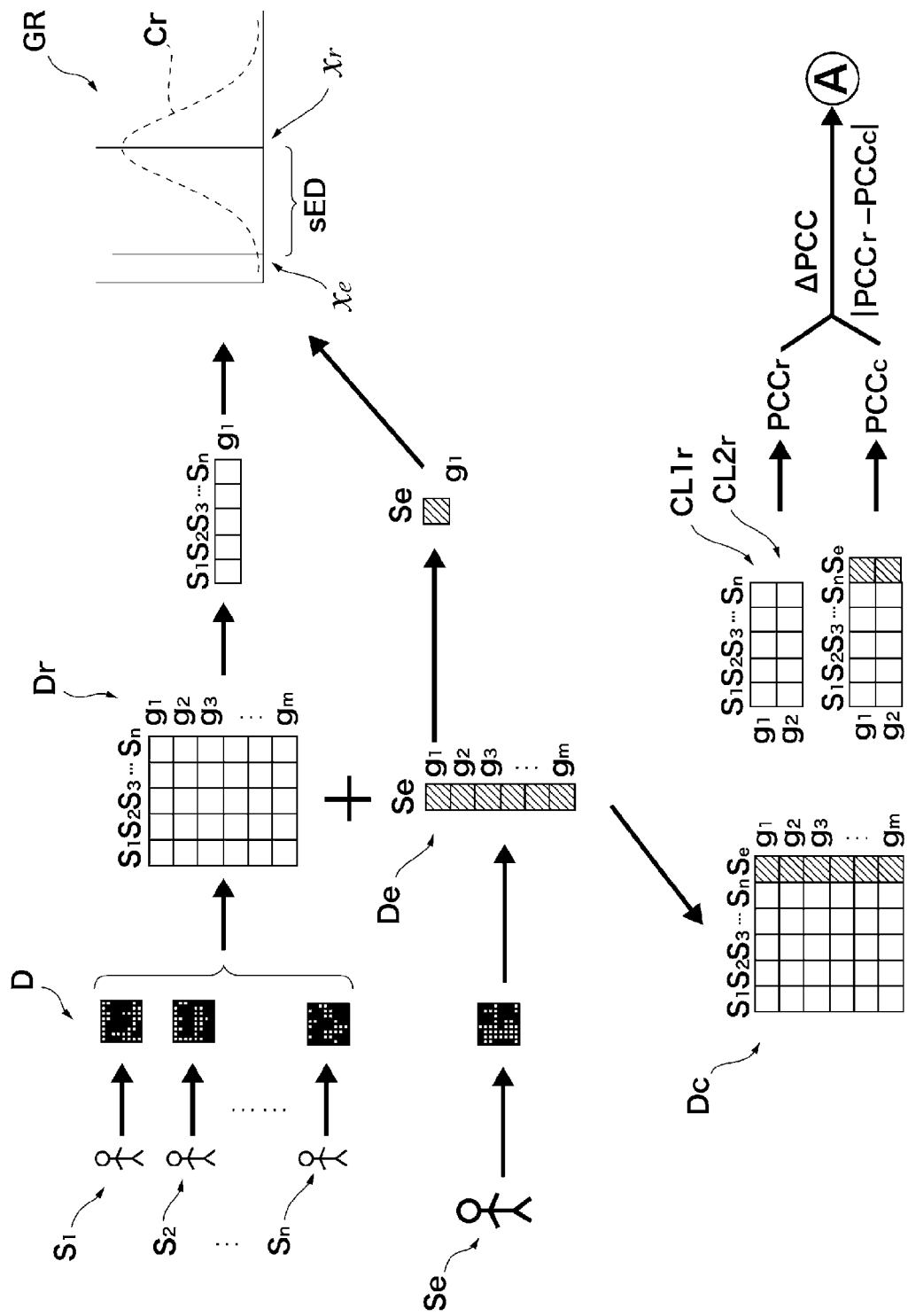
FIG. 3 is a schematic view illustrating the biomarker detection method according to the first embodiment of the present invention.

A biomarker detection method according to a first embodiment of the present invention will be described below with reference to FIG. 2 to FIG. 5. FIG. 2 is a flowchart illustrating the biomarker detection method according to the first embodiment, and FIG. 3 and FIG. 4 are schematic views illustrating the biomarker detection method according to the first embodiment.

As shown in FIG. 2, the biomarker detection method according to the first embodiment includes: a step of preparing a reference dataset (ST1); a step of generating an examination target dataset (ST2); a step of calculating a first correlation coefficient (ST3); a step of calculating a second correlation coefficient (ST4); a step of calculating a difference correlation coefficient (ST5); a step of acquiring an index (ST6); and a step of selecting a biomarker (ST7).

<Step of Preparing Reference Dataset (ST1)>

First, a reference dataset Dr (FIG. 3) is prepared. The reference dataset Dr is a set of data used as the data to be referred for detecting a biomarker. The reference dataset Dr is prepared by conducting biological measurement on each of a plurality of biological data providers S1, S2, . . . , Sn, that is, by conducting measurement on biological systems. Even though an examination subject Se (hereinafter referred to as a subject Se) of the biomarker detection method according to the first embodiment is normally not included in the biological data providers S1, S2, . . . , Sn, there may also be cases where the subject Se is included therein.

In the first embodiment, the biological data providers S1, S2, . . . , Sn are in good health, and biological samples (such as blood) are taken from those persons. Here, the biological data provider in good health may be a person who does not notice any symptoms and is not necessarily considered to be healthy by a medical checkup and other tests. However, a person who is found to have a high probability of getting a specific disease cannot be the biological data provider. The number of the biological data providers S1, S2, . . . , Sn is not specifically limited. However, at least 8 biological data providers are preferable, and 10 or more biological data providers are much preferable, for example.

Measurement and/or treatment are conducted on each of the biological samples, and data D (expression level) regarding genes g1, g2, . . . , gm as factor items is acquired in the first embodiment. In this case, the biological samples are preferable to be processed by a high throughput technology such as a DNA chip. With the high throughput technology, it is possible to measure the expression level of 20,000 genes or more from a single biological sample. The acquired data of the gene expression level is arranged in a matrix as illustrated in FIG. 3 for the sake of simplicity. Each square ( ) within the matrix reference dataset Dr schematically shows expression level data of the gene g1, expression level data of the gene g2, . . . , and expression level of the gene gm of the biological data provider S1.

<Step of Generating Examination Target Dataset (ST2)>

Then, a biological sample is also taken from the subject Se in the same manner to acquire a subject dataset De regarding genes g1, g2, g3, . . . , gm (FIG. 3). Thereafter, the reference dataset Dr prepared in advance is duplicated and the subject dataset De is added to the duplicated reference dataset Dr to generate an examination target dataset Dc.

<Step of Calculating First Correlation Coefficient (ST3)>

Then, correlation coefficients between data items within the reference dataset Dr are calculated. As can be seen from FIG. 3, there are n data corresponding to n members of biological data providers S1, S2, . . . , Sn regarding the gene g1 in the reference dataset Dr. Similarly, there are also n data regarding the gene g2. First, a correlation coefficient is calculated between a set CL1r of the gene g1 and a set CL2r of the gene g2. In the first embodiment, Pearson product-moment correlation coefficient (PCC) is calculated between the two sets. Subsequently, PCC is acquired between the set of the gene g1 and each of the sets of the genes g3, g4, . . . , and gm.

Further, PCC is acquired between the set of the gene g2 and each of the sets of the genes g3, g4, . . . , and gm, and between the set of the genes g3 and each of the sets of the genes g4, g5, . . . , and gm. In this manner, PCC is acquired between all pairs of the sets among the sets of the genes g1, g2, g3, . . . , gm. The correlation coefficient PCC acquired from the reference dataset Dr is referred to as PCCr for the sake of simplicity.

<Step of Calculating Second Correlation Coefficient (ST4)>

Then, correlation coefficients between the data items within the examination target dataset Dc are calculated. As shown in FIG. 3, the number of data items belonging to the set of each gene in the examination target dataset Dc is n+1 and the same method as the calculation method for the reference dataset Dr is used to calculate PCC regarding the examination target dataset Dc. The correlation coefficient PCC in the examination target dataset Dc is referred to as PCCc for the sake of simplicity.

<Step of Calculating Difference Correlation Coefficient (ST5)>

Thereafter, difference correlation coefficients of the above-described correlation coefficients PCCr and PCCc are calculated. That is, the difference correlation coefficient $\Delta PCC$ (absolute value of (PCCr−PCCc)) between the correlation coefficient PCCr between the set of the genes g1 and the set of the genes g2 of the reference dataset Dr and the correlation coefficient PCCc between the set of the first genes g1 and the set of the genes g2 of the examination target dataset Dc is calculated. Then, the difference correlation coefficient $\Delta PCC$ between the reference dataset Dr and the examination target dataset Dc is calculated regarding the correlation coefficient between (the set of) the gene g1 and (the set) of the gene g3. Subsequently, the difference correlation coefficient $\Delta PCC$ (FIG. 3) between the reference dataset Dr and the examination target dataset Dc is calculated regarding the correlation coefficients between the gene 1 and each of the genes g4, g5, . . . , gm. Similarly, the difference correlation coefficient $\Delta PCC$ is also calculated between the dataset Dr and dataset Dc regarding the correlation coefficients between the gene 2 and each of the genes g3, g4, . . . , gm. In this manner, the difference correlation coefficients $\Delta PCC$ are calculated for combinations corresponding to every two sets of genes between the reference dataset Dr and the examination target dataset Dc.

Then, $\Delta PCC$ exceeding a threshold value (which may be a fixed value or variable value) is extracted from $\Delta PCC$ calculated in this way. Here, it is assumed that a difference correlation coefficient network Nrc shown in FIG. 4 is constructed based on the selected $\Delta PCC$ for the sake of simplicity. For example, if the difference correlation coefficient $\Delta PCC$ between the correlation coefficient PCC of the gene g1 and the correlation coefficient PCC of the gene g2 is extracted, a node G1 corresponding to the gene g1 and a node G2 corresponding to the gene g2 are set up, and those nodes G1 and G2 are connected via a branch B (linked). The same operations are performed for all the extracted difference correlation coefficients $\Delta PCC$ to construct the difference correlation coefficient network Nrc (FIG. 4).

<Step of Acquiring Indexes (ST6)>

Next, average values of the correlation coefficients between other nodes are calculated for each node. First, an average value sPCCin of the correlation coefficients between a node of interest and primary nodes for that node is calculated. Here, the primary node is a node linked to the node of interest. For example, regarding the node G1 shown in FIG. 4, the nodes G2, G3, and G4 are linked to the node G1. Therefore, those nodes G2, G3, and G4 are the primary nodes of the node G1. The correlation coefficient between the nodes G1 and G2, the correlation coefficient between the nodes G1 and G3, and the correlation coefficient between the nodes G1 and G4 are averaged to acquire the average value sPCCin.

In addition, for example, the correlation coefficient between the nodes G1 and G2 corresponds to the previously calculated differential correlation coefficient ($\Delta PCC$) between the genes g1 and g2. That is, the average value sPCCin in this example is the average value of $\Delta PCC$ between the genes g1 and g2, $\Delta PCC$ between the genes g1 and g3, and $\Delta PCC$ between the genes g1 and g4.

Regarding the node G5 shown in FIG. 4, the node G5 is linked only to the node G2. In this case, not the average value but the correlation coefficient between the nodes G5 and G2 may be used as sPCCin.

Then, an average value sPCCout of the correlation coefficients between the primary and secondary nodes of the node of interest is calculated. Here, the secondary node is a node linked to the primary node of the node of interest, but not linked to the node of interest. Regarding the node G1 shown in FIG. 4, the nodes G5, G6, and G7 linked to the primary node G2, the node G8 linked to the primary node G3, and the nodes G9 and G10 directly linked to the primary node G4 correspond to the secondary nodes. Therefore, a total of six correlation coefficients between the primary node G2 and the secondary nodes G5, G6, and G7, between the primary node G3 and the secondary node G8, and between the primary node G4 and the secondary nodes G9 and G10 are averaged to acquire the average value sPCCout.

The correlation coefficient between the nodes G2 and G5, for example, corresponds to the difference correlation coefficient ΔPCC between the genes g2 and g5 corresponding to the nodes G2 and G5, respectively.

Now, referring back to FIG. 3. A graph GR has a horizontal axis representing the gene expression level and a vertical axis representing its probability. On the graph Gr, shown with a broken line is an expression level—probability curve Cr regarding gene g1 of the reference dataset Dr (that is, of a plurality of biological data providers S1, S2, ..., Sn). As shown in the graph GR, the probability of the expression levels of gene g1 of the plurality of biological data providers S1, S2, ..., Sn is almost normally distributed and an average value $\chi_r$ of the expression levels is acquired from the distribution chart. In addition, in the graph GR, the data (expression level) of gene g1 of the subject Se is also plotted with a solid line and if the expression level is defined as $\chi_e$, a difference sED from the average value $\chi_r$ can be acquired by $|\chi_r - \chi_e|$.

Next, an index (score) Is regarding the node G1 (that is, the gene g1) is acquired from the average value sPCCin, the average value sPCCout, and the difference sED according to following Equation (1).

$$Is = sED \times sPCCin / sPCCout \quad (1)$$

Then, the index Is is calculated for all the nodes G2, G3, ..., G10 in the same manner.

<Step of Selecting Biomarker (ST7)>

Then, as schematically shown in FIG. 4, a plurality of indexes Is calculated for all the nodes are sorted in descending order. Specified numbers of indexes Is are selected in descending order from the sorted indexes Is. Thereby, the genes corresponding to the specified numbers of selected indexes Is are detected as biomarkers. As shown in FIG. 4, it is also possible to define a threshold value Vth and select the indexes Is exceeding the threshold value Vth. Instead of calculating Indexes for all the nodes, the nodes having a specified sED value (for example, sED equal to or larger than a certain value) may be selected in advance and ΔPCC of the selected nodes may be calculated to acquire the indexes.

As described above, with the biomarker detection method according to the first embodiment, first, the correlation coefficients PCCr between the factor items of the reference dataset Dr acquired from the biological data providers S1, S2, ..., Sn are calculated, and the correlation coefficients PCCc between each of the factor items of the examination target dataset Dc acquired by adding the subject dataset De of the subject Se to the reference dataset Dr are calculated. Then, the difference correlation coefficients ΔPCC between them are acquired, and the difference correlation coefficients ΔPCC exceeding the threshold value are extracted therefrom and thereby the difference correlation coefficient network Nrc is constructed. For each of all the nodes of the difference correlation coefficient network Nrc, sPCCin and sPCCout are calculated. On the other hand, the difference sED between the average value of the reference dataset Dr and the examination target dataset Dc is acquired regarding each of the factor items. The indexes Is are calculated by Equation (1) including sED, sPCCin, and sPCCout, and the genes corresponding to the indexes Is exceeding the threshold value Vth are detected as the biomarkers.

The biomarkers are detected because the health state (although not apparent from the appearance) of the subject Se is different from (the average of) the biological data providers S1, S2, ..., Sn. It is clear from the fact that if the subject Se is in a good health state (point a) as in the case of the biological data providers, the difference correlation coefficient ΔPCC between the datasets Dr and Dc becomes almost zero, therefore the biomarker is not detected.

On the other hand, the critical state described above (point b in FIG. 1) is a state in which the subject himself has no particular subjective symptom, but may immediately shift to an early disease state. In such a state, it is generally known that system parameters fluctuate increasingly and there exist some parameters whose fluctuations are strongly correlated. In the critical state, the factor items showing a large difference between the reference dataset Dr and the examination dataset Dc are considered to correspond to biological factors that fluctuate increasingly and are strongly correlated in a transient state. Therefore, it is possible to determine that the subject Se is in the critical state based on the detection of the biomarker.

Figure 5:
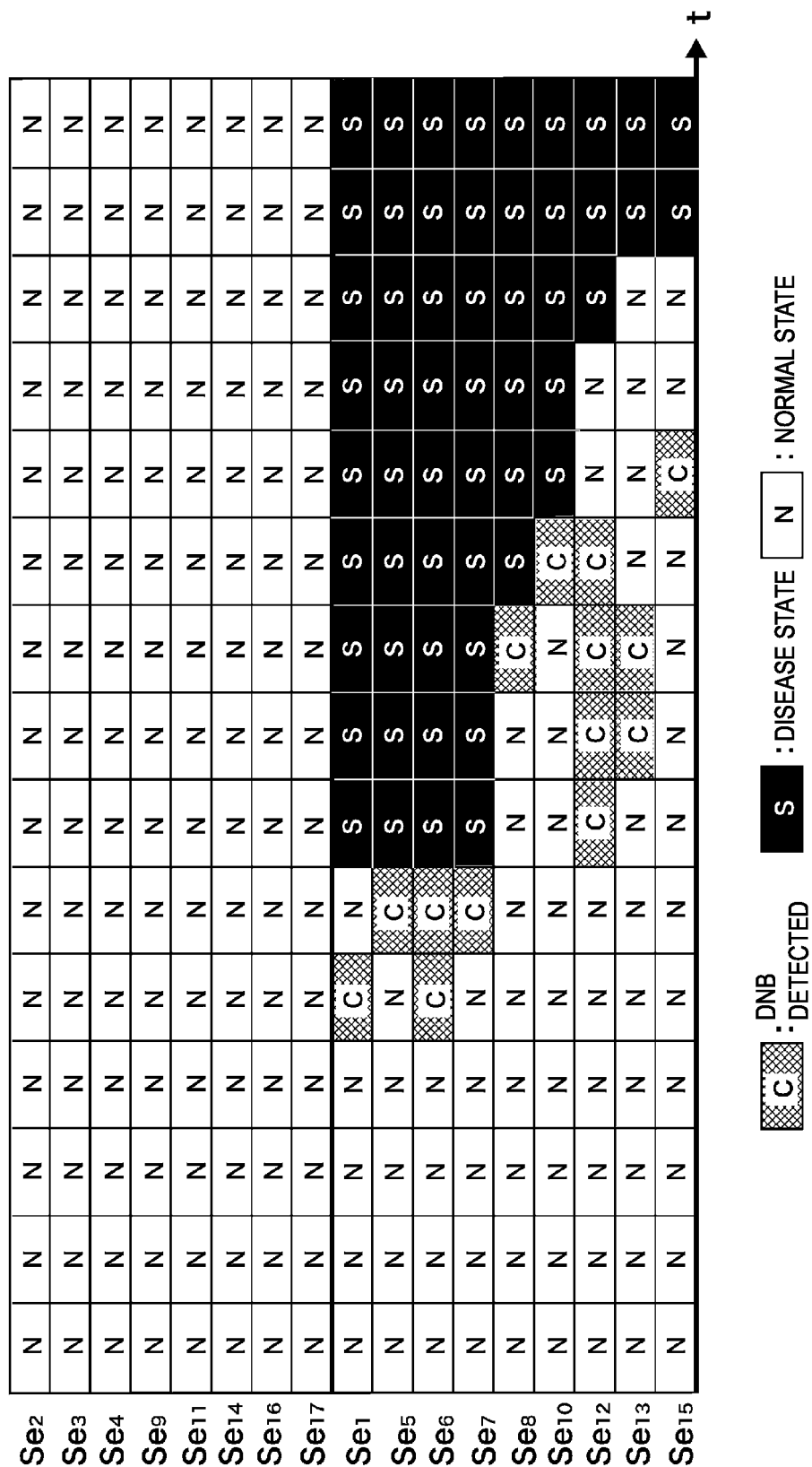
FIG. 5 is a table illustrating results of experiments conducted for verifying the biomarker detection method of the first embodiment.

Next, an experiment conducted for verifying the effect of the biomarker detection method according to the first embodiment will be described. In this experiment, 17 healthy subjects Se1 to Se17 were intranasally inoculated with influenza virus, and the biomarker detection method according to the first embodiment was conducted 15 times as time passes. FIG. 5 is a table showing the results of the experiment. "N" in the table indicates that the biomarker is not detected by the biomarker detection method according to the first embodiment, "C" indicates that the biomarker is detected by the biomarker detection method according to the first embodiment, and "S" indicates that the subject actually caught the influenza.

As can be seen from the table, the subjects Se2, Se3, etc. with no biomarker being detected were not in a disease state, and all the subjects Se1, Se5, etc. with the biomarker being detected subsequently came to be in a disease state. From the results, the beneficial effect of the biomarker detection method according to the first embodiment is evident.

In the experiment, detection of the biomarkers was conducted after the nasal inoculation of the influenza virus to the subjects, and the subjects having the biomarker being detected caught the influenza. Therefore, it can be said that a sign of influenza onset is found by detection of the biomarker. In general, however, detection of the biomarker suggests that the health state is transitory or there is a sign of onset of some kind of diseases, but it is not possible to identify a specific disease. If the corresponding factor item and the disease are associated with each other like the experiment of the influenza described above, it becomes possible to identify the disease that may develop later, upon detection of the biomarker. That is, the biomarker according to the first embodiment has an advantage of being able to become a sign for developing a specific disease.

Second Embodiment

Figure 6:
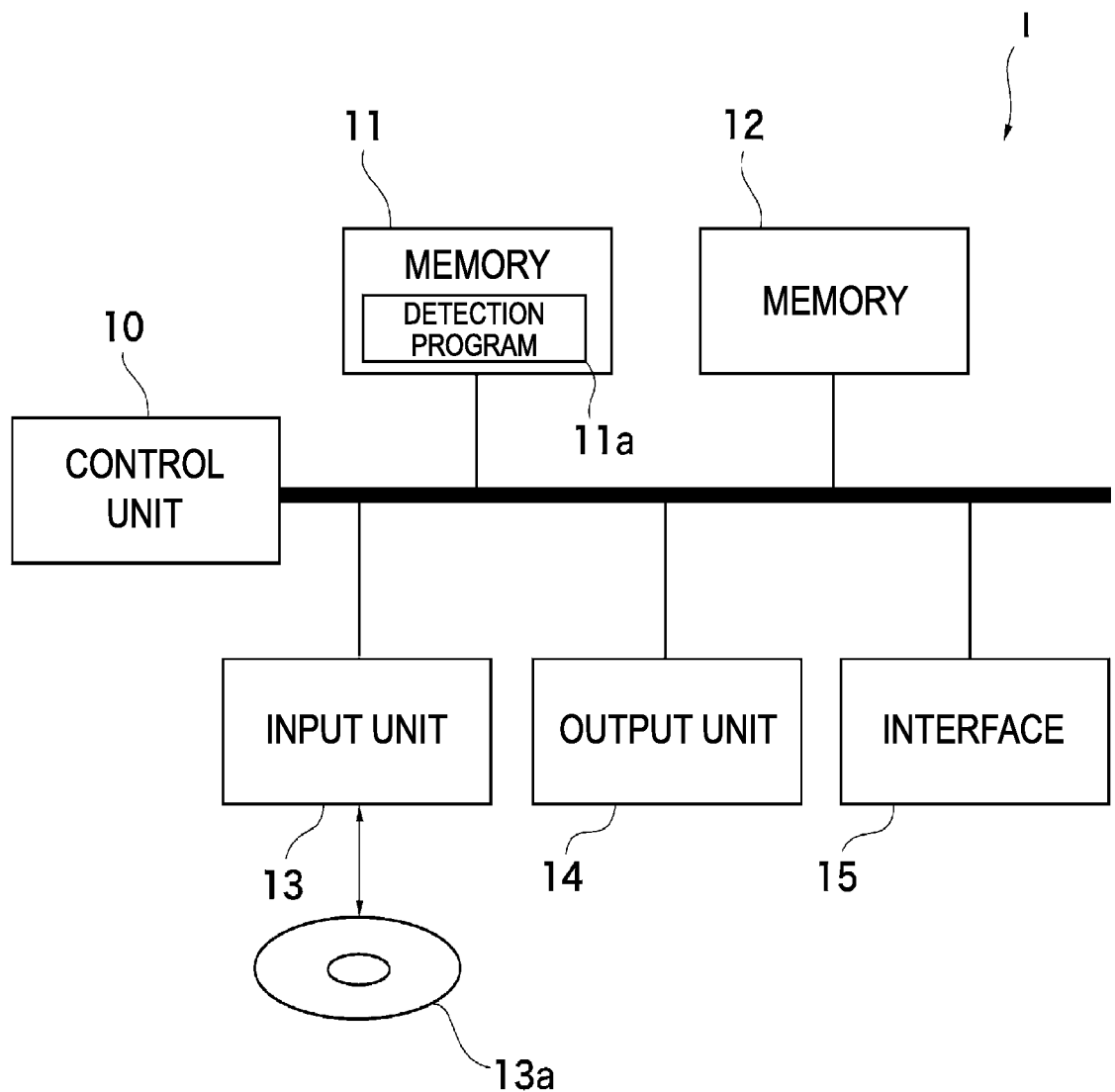
FIG. 6 is a block diagram illustrating a configuration of a biomarker detection device according to a second embodiment of the present invention.

Next, a biomarker detection device according to a second embodiment will be described. FIG. 6 is a block diagram illustrating an exemplary configuration of the detection device according to the second embodiment. The biomarker detection device 1 shown in FIG. 6 includes a control unit 10, a memory 11, a memory 12, an input unit 13, an output unit 14, and an interface 15.

The control unit 10 is configured by using a circuit such as a CPU (Central Processing Unit) and controls the entire detection device 1. The memory 11 includes a magnetic recording device such as an HDD (Hard Disk Drive) and a nonvolatile auxiliary recording device such as an SSD (Solid State Disk). Various kinds of programs such as a detection program 11a according to the embodiment of the present invention are recorded in the memory 11. The detection program 11a includes instructions (codes) for causing the detection device 1 to perform the biomarker detection method according to the first embodiment.

The detection program 11a can be stored in a computer readable medium 13a, and the detection program 11a can be installed in the memory 11 from the computer readable medium 13a via the input unit 13, for example. Here, the computer readable medium 13a may be non-transitory or tangible computer readable medium including an optical disk medium and a magnetic medium or the like such as a hard disk drive (HDD), a solid state drive (SDD), a random access memory (RAM), a read only memory (ROM), an erasable programmable read only memory (EPROM or flash memory device), a compact disk ROM (CD-ROM), and a digital versatile disc ROM (DVD-ROM).

The memory 11 can record the reference dataset Dr described in the first embodiment. The reference dataset Dr may be inputted and recorded to the memory 11 via the input unit 13 or may be inputted and recorded from, for example, an external database or the like via the interface 15.

The memory 12 includes volatile memories such as an SDRAM (Synchronous Dynamic Random Access Memory) and an SRAM (Static Random Access Memory). The memory 12 can store the subject dataset De (FIG. 3) described in the first embodiment. The subject dataset De may preferably be stored in the memory 12 via the input unit 13. The examination target dataset Dc (FIG. 3) described in the first embodiment can be generated by reading out the reference dataset Dr recorded in the memory 11 to the control unit 10, reading out the subject dataset De stored in the memory 12 to the control unit 10, and adding the subject dataset De to the reference dataset Dr by the control unit 10, for example. The generated examination target dataset Dc may be stored in the memory 12.

The input unit 13 includes hardware such as a keyboard, a mouse, and an input/output (I/O) device and software such as a driver. The I/O device can access to the computer readable medium 13a. The output unit 14 includes hardware such as a display and a printer and software such as a driver.

The interface 15 acquires various kinds of data from outside. Specifically, the interface 15 includes hardware such as a port to which a LAN (Local Area Network) cable is connected, to receive data via a communications network, and a port to which a dedicated cable such as a parallel cable connectable to a measurement device is connected, and software such as a driver.

The detection program 11a recorded in the memory 11 is stored in the memory 12 and executed based on control of the control unit 10 to function as the detection device 1 of the second embodiment.

While the memory 11 and the memory 12 are individually configured in the second embodiment, those memories may be configured with a single piece of hardware in other embodiments. That is, different areas of a single piece of hardware may be used as the memory 11 and the memory 12.

The control unit 10, the memory 11, the memory 12, the input unit 13, the output unit 14, and the interface 15 constituting the detection device 1 may be placed in a single housing or in the same place. Alternatively, each of the elements of the detection device 1 or a part of the elements may be placed in one or more housings in another place and connected via a wired or wireless network. Various kinds of processing executed by the detection device 1 may be executed by using cloud computing via a network such as the Internet.

Alternatively, a plurality of detection devices 1 may be provided to execute various kinds of processing including the above-described biomarker detection method in parallel. Alternatively, each element of the detection device 1 may include a plurality of units (such as two control units 10 and two memories 11) to execute various kinds of processing in parallel. Such parallel processing can increase the speed and, through having the data stored in parallel, the capacity and the speed can be increased. Furthermore, by executing the parallel processing while sharing the data between hospitals and inspection agencies other than the hospitals, examinations and diagnoses can be efficiently performed on a greater number of patients.

As described above, it is preferable for the biomarker detection method according to the first embodiment to use the high throughput technology and the device applicable to the high throughput technology. While there are more than 20,000 genes of humans, when the expression level regarding 20,000 genes (m=20,000) are used as the plurality of factor items, for example, $_{20000}C_2$ (=199,990,000) calculations need to be performed in each of the steps of: calculating the first correlation coefficients between the plurality of factor items (ST3); calculating the second correlation coefficients between the plurality of factor items (ST4); and calculating the difference correlation coefficients between the first correlation coefficients and the second correlation coefficients (ST5). Needless to say, it is impossible for humans to accurately perform such vast amount of calculations within reasonable time, and it is necessary to use a device capable of executing the vast amount of calculations accurately. Even if the calculations described above are performed by a plurality of persons, enormous amount of time is required (may take several years), so that the symptoms of the disease of the patients may get worse while the persons are performing the calculations. If so, it is not possible to achieve the purpose of detecting the critical state (state between healthy and diseased) before transiting to the disease state. Therefore, in order to achieve the biomarker detection method described above, it is necessary to use the detection device 1 that is capable executing the vast amount of calculations fast and accurately. This is also true for a device that executes a biomarker detection method according to a third embodiment and a device that executes a biomarker detection method according to a fourth embodiment as will be described later.

Third Embodiment

Figure 7:
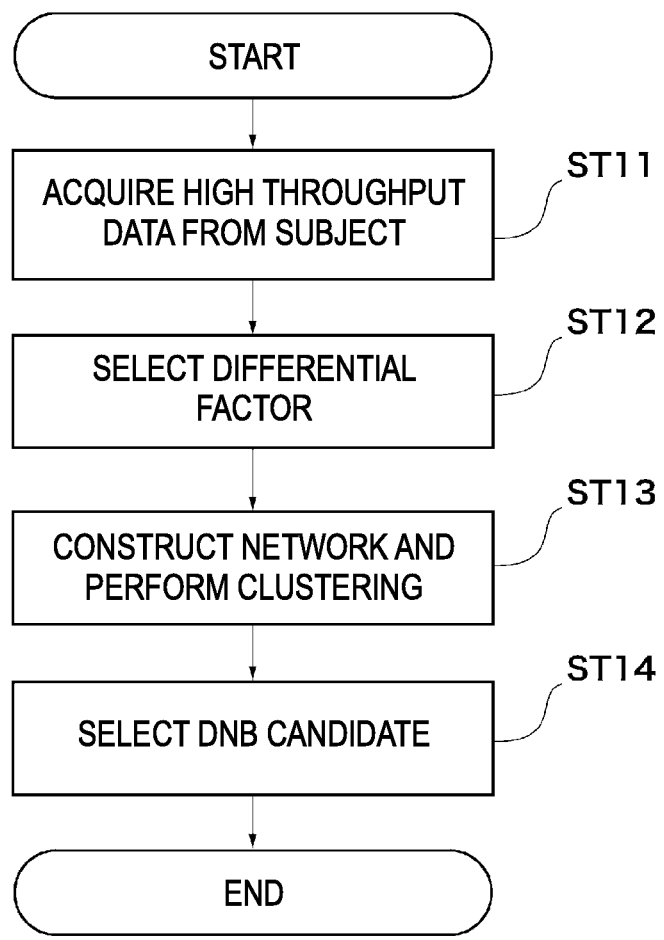
FIG. 7 is a flowchart illustrating a biomarker detection method according to a third embodiment of the present invention.

Next, the biomarker detection method according to the third embodiment will be described with reference to FIG. 7. FIG. 7 is a flowchart illustrating the biomarker detection method according to the third embodiment.

As shown in FIG. 7, the biomarker detection method according to the third embodiment includes: a step of acquiring high throughput data (ST11); a step of selecting differentially expressed factors (ST12); a step of performing clustering (ST13); and a step of selecting biomarkers (ST14).

To begin with, in the step of acquiring the high throughput data (ST11), the high throughput data at different time points are acquired from the subject Se. Specifically, first of all, biological samples are taken from the subject Se a plurality of times in time series. It is desirable to take the biological samples for five times or more, for example. Intervals between adjacent time points may be set as several days, several weeks, several months, or several years, or may be set as several minutes or several hours depending on the condition of disease.

From each of a plurality of biological samples acquired in the manner described above, gene expression levels as the factor items are acquired as the high throughput data by the high throughput technology.

Then, in the step of selecting the differentially expressed factors (ST12), the differentially expressed factors are selected from the acquired high throughput data. That is, differentially expressed genes are selected from the data of 20,000 genes or more acquired from a single biological sample by the high throughput technology. The differentially expressed gene is a gene exhibiting notable change in expression level. Specifically, selection of the differentially expressed genes is performed as follows. First, the biological sample taken in the first time among the plurality of biological samples is defined as a control sample. For the sake of simplicity, the data acquired from the control sample is referred to as Ddmc, and data of the gene of the biological sample taken in the second time is referred to as Ddm. Then, student's t-test is performed on the gene data Ddm to select the gene exhibiting notable change in the expression level with respect to the data Ddms of the control sample. For the sake of simplicity, such gene is referred to as Ddm1.

While the student's t-test is used for selecting the gene Ddm1 in the third embodiment, it is also possible to apply other test methods such as Mann-Whitney U test, for example, in other embodiments. The tests by such nonparametric methods are particularly effective when Ddm as population does not follow normal distribution. In a case of performing student's t-test, it is possible to set values of 0.05, 0.01, or the like as appropriate for the value of significance level $\alpha$.

Then, in the step of performing clustering (ST13), the differentially expressed factors (differentially expressed genes) selected in the step of selecting the differentially expressed factors (ST12) are classified into a plurality of clusters.

In this step (ST12), first, multiple comparisons are performed on the gene Ddm1 exhibiting notable change in the expression level with respect to the data Ddmc of the control sample by using a false discovery rate FDR or by correcting a plurality of student's t-tests to acquire genes Ddm2 (not shown). Then, the genes exhibiting relatively notable change in standard deviation SD are selected as differentially expressed genes Dsm (FIG. 8) from the genes Ddm2 by using a two-fold change method (ST12). The differentially expressed genes Dsm selected herein not only exhibit a notable difference compared with the data Ddmc of the control sample but also deviate greatly from the average value of themselves.

Then, correlation coefficients between the differentially expressed genes Dsm are calculated. For the sake of simplicity, let us now assume that genes gn1, gn2, gn3, . . . , gnp are selected as the differentially expressed genes Dsm. Further, assuming that the data (expression levels) of the gene gn1 at time points t1, t2, t3, . . . , tp of taking the biological samples are respectively denoted by gn11, gn12, gn13, . . . , gn1p in order, a set of p elements CL1m {gn11, gn12, gn13, . . . , gn1p} is acquired. Similarly, assuming that the expression levels of the gene gn2 at the time points t1, t2, t3, . . . , tp of taking the biological samples are respectively denoted by gn21, gn22, gn23, . . . , gn2p, a set of p elements CL2m {gn21, gn22, gn23, . . . , gn2p} is acquired. Similarly, sets CL3m, . . . , CLpm are also acquired for other genes gn3, . . . , gnp, respectively.

Figure 8:
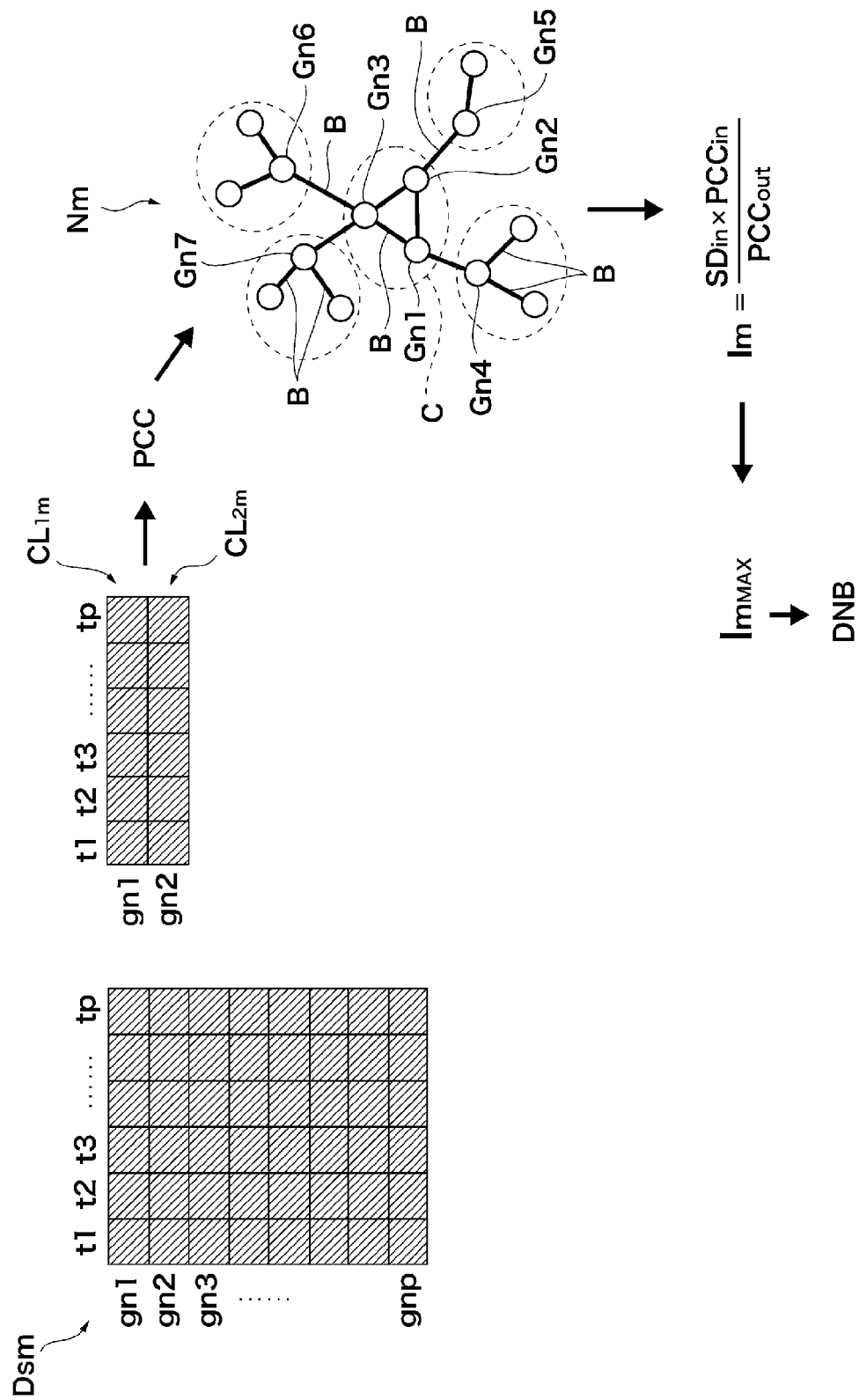
FIG. 8 is a schematic view illustrating the biomarker detection method according to the third embodiment of the present invention.

Then, correlation coefficients are calculated between all the pairs of sets among all the gene sets CL1m, Cl2m, CL3m, . . . , CLpm. The correlation coefficients may be Pearson correlation coefficients (PCC). Among the calculated correlation coefficients PCC, those PCCs exceeding a threshold value are selected and a network is constructed, for example, based on the selected PCCs. For example, when the correlation coefficient PCC between the sets CL1m and CL2m exceeds the threshold value, the node Gn1 corresponding to the gene gn1 and the node Gn2 corresponding to the gene gn2 are set and those nodes Gn1 and Gn2 are linked via a branch B. The same operation is performed for all the PCC exceeding the threshold value, and a network Nm shown in FIG. 8 is constructed.

Thereafter, the nodes in the network Nm are clustered. That is, a plurality of nodes are classified into groups (clusters). Clustering herein is processing for classifying each of a plurality of biomolecules highly correlated with each other into groups, and each of the groups the biomolecules are classified is referred to as a cluster. That is, the differentially expressed genes Dsm described above are classified into n clusters so as to put the molecules highly correlated with each other in a single cluster. Referring to FIG. 8, shown are five clusters sectioned by dotted lines, and two or three nodes are included in each cluster. Note, however, that the number of clusters and the number of nodes included in the clusters are not limited to the case of FIG. 8 and may be determined as appropriate. For example, the number of clusters may be three or more in total, and five or more nodes may be included in a single cluster.

Then, in the step of selecting candidates for the biomarkers (ST14), a cluster is selected as the biomarker from the plurality of clusters acquired in the step of performing clustering (ST13) which shows the most prominent increase in the correlation between the factor items inside the cluster, shows the most prominent increase in the standard deviation of the factor items inside the cluster, and shows the most prominent decrease in the correlation between the factor items inside the cluster and the factor items outside the cluster.

Specifically, the average value PCCin (hereinafter referred to as internal PCC average value) of the correlation coefficients between the nodes inside the cluster are calculated for each cluster, the average value PCCout (hereinafter referred to as internal and external PCC average value) of the correlation coefficients between the nodes inside the cluster and the nodes outside the cluster are calculated, and the standard deviation SDin of the nodes inside is calculated. Referring to FIG. 8, a cluster C including the nodes Gn1, Gn2, and Gn3 is formed. Concerning the cluster C, the correlation coefficient between the nodes Gn1 and Gn2 inside the cluster C (that is, the correlation coefficient PCC between the genes gn1 and gn2), the correlation coefficient between the nodes Gn2 and Gn3 (the correlation coefficient PCC between the genes gn2 and gn3), and the correlation coefficient between the nodes Gn3 and Gn1 (the correlation coefficient PCC between the genes gn3 and gn1) are averaged to acquire the internal PCC average value PCCin.

Subsequently, the internal and external PCC average value PCCout is acquired by leveling a total of four correlation coefficients that are: the coefficient between the node Gn1 and the node Gn4 that is directly connected thereto but is outside the cluster C (the correlation coefficient PCC between the genes gn1 and gn4); the coefficient between the node Gn2 and the node Gn5 that is directly connected thereto but is outside the cluster C (the correlation coefficient PCC between the genes gn2 and gn5); and the correlation coefficients between the node Gn3 and each of the nodes Gn6 and Gn7 which are directly connected thereto but are outside the cluster C (the correlation coefficient PCC between the genes gn3 and gn6 and the correlation coefficient PCC between the genes gn3 and gn7).

Further, the standard deviation SDin of the data (expression levels) of the genes gn1, gn2, and gn3 corresponding, respectively, to the nodes Gn1, Gn2, and Gn3 inside the cluster C is calculated.

Index Im of the cluster C is calculated according to the following Equation (2) from the internal PCC average value PCCin, the internal and external PCC average value PCCout, and the standard deviation SDin acquired in the manner described above.

$$Im = SDin \times PCCin / PCCout \qquad (2)$$

Subsequently, the same calculations are performed for all the clusters, and the cluster (or the gene group corresponding to the nodes belonging to the cluster) that provides the largest index Im is selected as the biomarker.

It is also possible to change the number of clusters and the number of nodes included in the clusters for the same nodes (group) and repeat the same calculations a plurality of times to find the cluster that provides a larger index Im.

It is also possible to perform significance test on the index Im of each cluster to determine whether or not the cluster is the biomarker.

It may be possible to calculate the indexes for each of the genes without performing clustering and calculate the indexes by using the standard deviation SD obtained when selecting the differentially expressed genes Dsm in step ST12 described above. Specifically, indexes It may be acquired according to following Equation (3) that is acquired by replacing sED of the molecules of Equation (1) described above with the standard deviation SD.

$$It = SD \times sPCCin / sPCout \qquad (3)$$

A plurality of indexes It calculated for all the nodes (differentially expressed genes Dsm) are sorted in descending order, and specified numbers of indexes It are selected in descending order from the sorted indexes It. Thereby, the genes corresponding to the specified numbers of selected indexes It are detected as the biomarkers.

As described above, with the biomarker detection method according to the third embodiment, the gene data (expression levels) is acquired from a plurality of biological samples taken from the subject Se in time series, and the differentially expressed genes Dsm are selected therefrom. The correlation coefficients PCC regarding the differentially expressed genes Dsm are acquired, and the network Nm is constructed based on the correlation coefficients PCC. The nodes configuring the network Nm are grouped into the clusters, the index Im is calculated for each of the clusters, and the genes corresponding to the nodes included in the cluster with the maximum value of the index are selected as the biomarkers.

In a case of calculating the indexes for each of the genes without performing clustering, the indexes It can be calculated by Equation (3) described above using the standard deviation SD calculated when selecting the differentially expressed genes Dsm (step ST12). The standard deviation SD is a variable indicating that the expression level of the gene of interest is increased or drastically increased. Hence, the standard deviation SD can be a substitute for sED in Equation (1).

It is possible with the third embodiment to acquire a plurality of nodes highly correlated with each other because: the differentially expressed factors (the genes Dsm exhibiting notable change in the expression level) are selected, the correlation coefficients between them are calculated and clustered, and the cluster with the maximum index Im is selected from the clusters as the biomarker; or when clustering is not performed and the indexes are calculated for each of the genes, the indexes It (Equation (3)) are calculated by using the standard deviation SD calculated when selecting the differentially expressed factors, and one or more specified numbers of indexes It are selected in descending order, thereby a plurality of nodes which are strongly correlated with each other are acquired. In a critical state, biological factors fluctuate increasingly and there exist some biological factors whose fluctuations are strongly correlated, as is known in the art. Therefore, the detection of the biomarker by the method of the third embodiment suggests that the subject Se is in a critical state.

Fourth Embodiment

Next, a biomarker detection method according to a fourth embodiment will be described with reference to FIG. 9. The biomarker detection method according to the fourth embodiment is different from the biomarker detection method according to the first embodiment in regards to the number of times the biological samples of the subject Se are taken. Specifically, while the biological samples of the subject Se are taken once in the biomarker detection method of the first embodiment, the samples are taken a plurality of times in time series in the biomarker detection method of the fourth embodiment. Hereinafter, the biomarker detection method of the fourth embodiment will be described concentrating on the differences.

Figure 9:
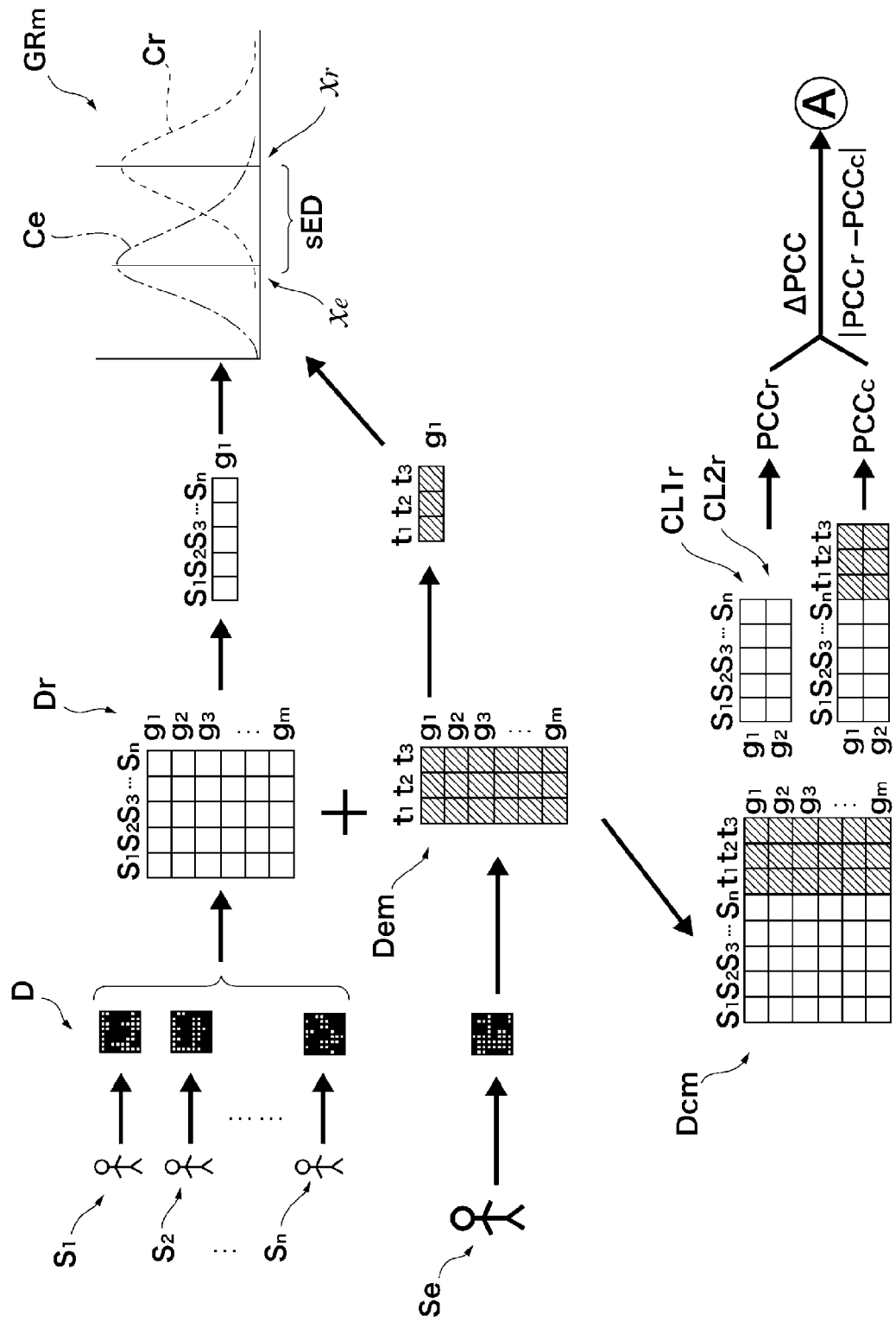
FIG. 9 is a schematic view illustrating a biomarker detection method according to a fourth embodiment of the present invention.

Referring to FIG. 9, a subject dataset Dem acquired from the biological samples taken from the subject Se at different time points t1, t2, and t3 is acquired. The number of times for taking the biological samples is set as three times for the sake of simplicity, but it is desirable to be five times or more, for example. Intervals between each time may be set as several days, several weeks, several months, or several years, or may be set as several minutes or several hours depending on the condition of disease.

The subject dataset Dem is added to the reference dataset Dr prepared in advance similarly to the first embodiment to generate the examination target dataset Dcm. In this example, the number of data items belonging to the set of each gene in the examination target dataset Dcm is n+3.

Then, similarly to the step of calculating the first correlation coefficients (ST3) and the step of calculating the second correlation coefficients (ST4) according to the first embodiment, the correlation coefficients PCCr between the data items in the reference dataset Dr and the correlation coefficients PCCc between the data items in the examination target dataset Dcm are calculated, and the difference correlation coefficients ΔPCC between them are calculated. Then, similarly to the step of calculating the difference correlation coefficients (ST5) according to the first embodiment, those APCC exceeding a threshold value are extracted from the calculated APCC, and a difference correlation coefficient network Nrc shown in FIG. 4 is constructed.

Regarding the difference correlation coefficient network Nrc, similarly to the step of acquiring the indexes (ST6) according to the first embodiment, the average value sPCCin of the correlation coefficients between the node of interest and the primary nodes and the average value sPCCout of the correlation coefficients between the primary and secondary nodes for the node of interest are acquired.

Referring to FIG. 9, an expression level—probability curve regarding the gene g1 is shown on a graph GRm with a broken line. On the graph, shown are the expression level—probability curve Cr regarding the gene g1 in the reference dataset Dr and an expression level—probability curve Ce regarding the gene g1 in the subject dataset Dem. The average value $\chi_r$ denotes the average value of the expression level—probability curve Cr, and the average value $\chi_e$ denotes the average value of the expression level—probability curve Ce. From the graph, a difference sED ($|\chi_r-\chi_e|$) between the average value $\chi_r$ and the average value $\chi_e$ is acquired.

Then, according to Equation (1) described above, the index Is regarding the node G1 (that is, the gene g1) is acquired from the average value sPCCin, the average value sPCCout, and the difference sED.

Then, the indexes Is are also calculated in the same manner regarding all the nodes G2, G3, . . . , G10 (that is, corresponding genes g2, g3, . . . , g10).

Then, as schematically shown in FIG. 4, a plurality of indexes Is calculated for all the nodes are sorted in descending order. Specified numbers of indexes Is are selected in descending order from the sorted indexes Is. The genes corresponding to the specified numbers of selected indexes Is are detected as the biomarkers. The number of selected indexes Is may be determined by defining a threshold value to select the index Is exceeding the threshold value.

By the biomarker detection method according to the fourth embodiment, the difference correlation coefficients ΔPCC between the correlation coefficients PCCr between the factor items of the reference dataset Dr and the correlation coefficients PCCc between the factor items of the examination target dataset Dcm are also acquired, and the biomarkers are detected from the indexes based on the difference correlation coefficients. Therefore, the same effects as those of the biomarker detection method according to the first embodiment can be exhibited.

By using the biomarkers detected by the biomarker detection method or the detection device according to the embodiments described above, it is possible to make a determination regarding a disease (i.e., to determine a pre-disease state immediately preceding a disease state or a state immediately preceding recovery from a disease). Examinations are performed on a person as a target of such determination to take biological samples, biomarkers are acquired by calculations from the biological samples, and the acquired biomarkers are compared with the already detected biomarkers. For example, determination is made as to whether or not the acquired biomarkers are included in the already detected group of genes of the biomarkers corresponding to a specific disease (higher-order gene group or the gene group specified in advance, and there may only be a single gene included in the gene group).

Such determination may be made automatically by the biomarker detection device and others according to the second embodiment or may be made by medical doctors, for example.

When it is determined that the biomarker or gene corresponds to the disease based on the determination result, information related to the disease may be presented.

Thereby, it is possible to determine whether the person is in a pre-disease state immediately preceding a disease or in a state immediately preceding recovery from a disease.

While some embodiments of the biomarker detection method, the biomarker detection device, and the biomarker detection program according to the present invention have been described heretofore, the invention is not limited to those embodiments but various modifications and changes are possible within the scope of the appended claims.

For example, while the reference dataset Dr is prepared before taking the biological samples of the subject Se in the first and fourth embodiments, the reference dataset Dr may be prepared after taking the biological samples of the subject Se or after acquiring the subject dataset De regarding the genes g1, g2, g3, . . . , gm from the biological samples in other embodiments. Also, the reference dataset Dr may be generated in advance and registered to a database. In this way, the reference dataset Dr can be prepared as necessary by being downloaded to the memory 11 from the database via the interface 15.

While the index Is is calculated according to Equation (1) in the first and fourth embodiments, the inventors found that the biomarker can be selected even when the denominator (sPCCout) of the equation is "1" (that is, even when the index Is is calculated based only on the numerator).

According to the first and fourth embodiments, it is possible to check whether or not the subject Se is in a critical health state on the assumption that the subject appears to be in good health. Oppositely, it is also possible to assume in other embodiments that the subject Se has a specific disease. In this case, patients who have the same disease as the subject Se can be the biological data providers S1, S2, . . . , Sn. In such case, when the biomarker is detected from the subject Se, it is estimated that the health of the subject Se is in a critical state toward a good state (point a of FIG. 1) from a disease state (point d or c on FIG. 1) and that the subject Se is heading for recovery. The specific disease is not limited to a certain disease but may be any diseases.

When the subject Se has a specific disease and is receiving specific medical treatment for the disease, patients receiving the same medical treatment can be the biological data providers S1, S2, . . . , Sn. When the biomarker is detected from the subject Se in such case, it is estimated that the medical treatment is effective for the subject Se and it is in a critical state toward a good state (point a of FIG. 1) from a disease state (point d or c on FIG. 1) and that the subject Se is heading for recovery.

Figure 1:
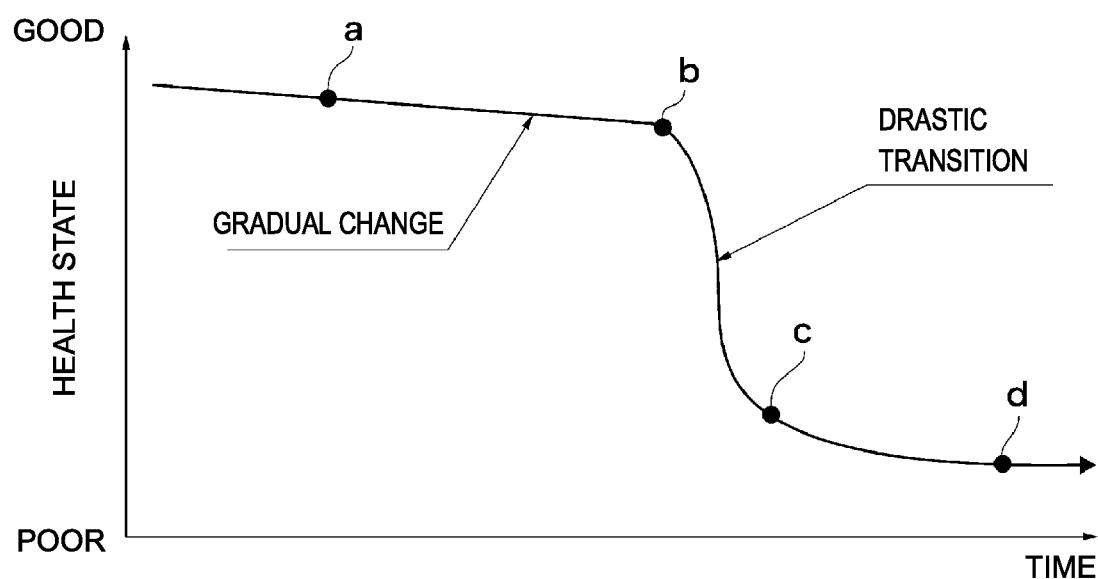
FIG. 1 is a schematic view illustrating a transition process from a good health state to a disease state.

In the third embodiment, when the biomarker is detected from the subject Se in good health, it is found that the health of the subject Se is in a critical state (point b of FIG. 1) toward a disease state (point d or c of FIG. 1) from a good state (point a of FIG. 1). Oppositely, when the biomarker is detected in a case where the subject Se is in a disease state, it is estimated that the subject Se is in a critical state and that the subject Se is heading for recovery.

Even when the subject Se is in a disease state as described above and the patient cannot feel the improvement in the medical condition or there is no improvement recognized in the medical condition with conventional examinations, it is possible with the biomarker detection method according to the embodiments of the present invention to check whether or not the medicine is working. Therefore, it is possible to correctly determine whether or not to continue the medical treatment.

Also, there may be cases where it takes a long period until the improvement in the medical condition is recognized depending on the conventional examinations. In such case, when it is found after a long period that there is no effect of the medicine, the medical condition may be deteriorated during that period. The use of the biomarker detection method according to the embodiments of the present invention makes it possible to grasp the sign of state transition at an early stage, so that it is possible to determine whether or not there is an effect of the medicine in a short period after starting the use of the medicine. Therefore, when there is no effect of the medicine, unuseful medical treatment can be avoided and it is possible to switch to other medical treatment methods at an early stage, thereby making it possible to delay the progression of disease or improve the medical condition. It is also possible to avoid uselessly using expensive medical drugs over a long period of time, thus suppressing the medical costs.

The biomarker detection method according to the fourth embodiment may be performed by the biomarker detection device 1 according to the second embodiment. In such case, the biomarker detection program causing the detection device 1 to execute the biomarker detection method according to the fourth embodiment may be recorded in the memory 11. Also, the detection program may be recorded in a non-transitory or tangible computer readable medium.

While the subject dataset Dem is generated from a plurality of data items acquired in time series from the biological samples of the subject Se and added to the reference dataset Dr to generate the examination target dataset Dcm in the fourth embodiment, it is also possible to use the individual data acquired at different time points in other embodiments. That is, every time the biological sample is taken at different time points, the biomarker detection method according to the first embodiment may be performed. More specifically, the biomarker detection method according to the first embodiment may be performed when taking the biological sample from the subject Se at the time point t1, and may be repeated at each of the time points t2, t3, . . . . Such detection method can also be performed with the detection device 1 described above by the detection program, and the detection program may be recorded in a non-transitory or tangible computer readable medium.

Although the difference correlation coefficient network Nrc or the network Nm is constructed in the first, third, and fourth embodiments, the correlation coefficients between the nodes can be calculated without constructing the network. Therefore, it is not essential to construct the network.

Although the indexes Is for the difference correlation coefficient network Nrc is calculated by using Equation (1) in the first and fourth embodiments, it is also possible to cluster the nodes on the difference correlation coefficient network Nrc, calculate the indexes Im according to Equation (2), and select the biomarker.

That is, there are a total of four types of biomarker detection methods that are: the case of calculating the indexes Is regarding the difference correlation coefficient network Nrc by using Equation (1) in the biomarker detection methods according to the first and fourth embodiments; the case of clustering the nodes of the difference correlation coefficient network Nrc and calculating the indexes Im according to Equation (2); the case of calculating the indexes Is by using Equation (1) for the network Nm constructed based on the correlation coefficients PCC regarding the differentially expressed genes Dsm in the biomarker detection method according to the third embodiment; and the case of clustering the nodes of the network Nm and calculating the indexes Im according to Equation (2).

Further, while the differentially expressed factors are selected from the high throughput data acquired by the high throughput technology in the third embodiment, the differentially expressed factors may also be selected in the first and fourth embodiments. Also, by using sED described above, factors having sED equal to or more than a specified value may be selected as the differentially expressed factors.

While (expression level of) genes are used as factor items in the above embodiments for the sake of simplicity, it is also possible to use not only genes but also numerical values of specified examination items (measurement items such as protein, cholesterol, blood sugar level, measurement items regarding metabolite, and others) in a blood test. In a case of taking the biological samples and extracting the factor items from the biological samples, the biological samples are not limited to be blood but may also be saliva, perspiration, and excrement such as urine or feces or may also be biological tissues (for example, liver tissues in a case of hepatic disorder). Furthermore, it is also possible to use numerical values and the like acquired by quantifying signals of electrocardiography, electroencephalography, computed tomography (CT), (nuclear) magnetic resonance imaging (MRI), and PET (Position Emission Tomography) image and others. Moreover, it is also possible to use numerical values and the like acquired by quantifying measurement values of sounds generated from the interior of the body such as voice or cardiac sound. The term "factor item" used in the above description is the item that can be the node of the network described above.

The biomarker detection method according to the present invention can be performed in general hospitals, academic medical centers, and others, and may also be performed by examination laboratories outside the hospitals, private enterprises and others providing blood diagnosis service and genetic diagnosis services for individuals. Needless to say, the biomarker detection device and the detection program according to the present invention can be employed in such examination laboratories, enterprises, and others.

The biomarker detection method, detection device, and detection program according to the present invention can be applied not only to humans but also to biological systems in general such as animals.

Conventionally, there are biomarkers as the indexes used for diagnosing a disease state. The biomarkers are used for discriminating a good state (within a reference value) and a disease state (outside the reference value) and for checking changes (improvement or deterioration) in the disease state. In contrast, the biomarker detection method according to the present invention is capable of detecting the sign of transition (critical state) from the good state to the disease state. That is, there is an advantage in the biomarker detection method according to the present invention that it is possible to avoid having a disease at an early stage.

The conventional biomarkers are chemical substances included in body fluids such as serum or urine or tissues taken from living bodies, and can be specified by molecular formulae or properties. In contrast, the biomarker according to the present invention varies depending on the subjects and diseases, and emerges after being detected. Hence, it is almost impossible and not practical to directly specify the biomarker by configuration (such as molecular formulae) or properties. Therefore, the biomarker according to the present invention is different from the conventional biomarkers.

In other words, the biomarker according to another embodiment of the present invention is a biomarker detected by the biomarker detection method that detects the biomarker to be an index of a state of a living body based on data acquired by performing measurement regarding the living body, the method including the steps of: preparing a reference dataset based on the data acquired from each of a plurality of reference living bodies; generating a target dataset by adding target biological data acquired from the target living bodies to the reference dataset; acquiring first correlation coefficients between a plurality of factor items in the reference dataset; acquiring second correlation coefficients between a plurality of factor items in the target dataset; acquiring difference correlation coefficients that are differences between the first correlation coefficients and the second correlation coefficients; acquiring indexes based on the difference correlation coefficients for each of the plurality of factor items; and selecting the biomarker based in the indexes.

The biomarker detection method and the biomarker detection program according to the embodiments described above specifically find the indexes indicating that the subject is in a critical state (indicating the sign of a disease state), and are different from conventionally known ordinary biological data processing simply executed by a computer.

Also, the biomarker described heretofore may also be referred to as a dynamic network biomarker (DNB).

REFERENCE SIGNS LIST

D Data
Dc, Dcm Examination target dataset
De, Dem Subject dataset
Dr Reference dataset
g1, g2, . . . , gm Gene
G1, G2, G3, G4, . . . , G10 Node
Nrc, Nm Difference correlation coefficient network
Se Subject
S1, S2, . . . , Sn Biological data provider
1 Detection device
10 Control unit
11 Memory
11a Detection program
12 Memory
13 Input unit
13a Computer readable medium
14 output unit
15 Interface

The invention claimed is:

1. A method for detecting a biomarker indicating a critical state before transiting to a disease state of a target biological system based on data acquired by measuring the target biological system, the method comprising the steps of:
preparing a reference dataset based on data acquired from a plurality of reference biological systems;
generating a target dataset by adding, to the reference dataset, target biological data acquired from the target biological system;
acquiring first correlation coefficients between a plurality of factor items in the reference dataset;
acquiring second correlation coefficients between the plurality of factor items in the target dataset;
acquiring difference correlation coefficients that are differences between the first correlation coefficients and the second correlation coefficients;
acquiring a first average value of the difference correlation coefficients between one factor item in the target biological data and a first one or more factor items having a prescribed correlation coefficient with respect to the one factor item, among the plurality of factor items;
acquiring an average value of a plurality of data items for the one factor item among the plurality of factor items in the reference dataset;
acquiring a difference between the average value and data of the one factor item in the target biological data;
acquiring each of indexes based on the difference and the first average value; and
detecting a factor item as a new biomarker indicating the critical state before transiting to the disease state of the target biological system based on the indexes.

2. The method according to claim 1, wherein
the step of acquiring each of the indexes comprises:
acquiring a second average value of the difference correlation coefficients between the first one or more factor items and a second one or more factor items having a prescribed correlation coefficient with respect to the first one or more factor items, amongst the plurality of factor items, wherein the second one or more factor items does not comprise the one factor item; and
acquiring each of the indexes by the equation given by (the difference×the first average value)/(the second average value).

3. The method according to claim 1, wherein
the step of detecting the biomarker comprises selecting, as the biomarker, a factor item corresponding to one or more specified numbers of the indexes in descending order when the indexes respectively acquired for the plurality of factor items are arranged in descending order.

4. The method according to claim 1, wherein
the data acquired from the plurality of reference biological systems is data acquired from the plurality of reference biological systems who are in good health.

5. The method according to claim 1, wherein
the data acquired from the plurality of reference biological systems is data acquired from the plurality of reference biological systems having a specific disease.

6. The method according to claim 1, wherein
the step of generating the target dataset further comprises adding, to the reference dataset, data of the plurality of factor items in the target biological data acquired a plurality of times from the target biological system, thereby generating the target dataset.

7. A disease assessment method comprising:
detecting the biomarker by using the method according to claim 1; and
determining whether the biomarker corresponds to a specific disease.

8. The method according to claim 1, wherein the plurality of factor items in the reference dataset and the target dataset comprise genes, measurement items in a blood test, and/or an item that can be a node in a network.

9. A biomarker detection device for detecting a biomarker indicating a critical state before transitioning to a disease state of a target biological system based on data acquired by measuring the target biological system, the biomarker detection device comprising:
a first memory configured to store a reference dataset prepared based on data acquired from a plurality of reference biological systems;

a second memory configured to store a target dataset generated by adding, to the reference dataset, target biological data acquired from the target biological system; and a processor configured to:
acquire first correlation coefficients between a plurality of factor items in the reference dataset;
acquire second correlation coefficients between the plurality of factor items in the target dataset;
acquire difference correlation coefficients that are differences between the first correlation coefficients and the second correlation coefficients;
acquire a first average value of the difference correlation coefficients between one factor item in the target biological data and a first one or more factor items having a prescribed correlation coefficient with respect to the one factor item, among the plurality of factor items;
acquire an average value of a plurality of data items for the one factor item among the plurality of factor items in the reference dataset;
acquire a difference between the average value and data of the one factor item in the target biological data;
acquire each of indexes based on the difference and the first average value; and
detect a factor item corresponding to the indexes as a new biomarker indicating the critical state before transitioning to the disease state of the target biological system.

10. The device according to claim 9, a processor further configured to:
acquire a second average value of the difference correlation coefficients between the first one or more factor item and a second one or more factor items having a prescribed correlation coefficient with respect to the first one or more factor items, among the plurality of factor items, wherein the second one or more factor items does not comprise the one factor item; and
acquiring each of indexes by an equation given by (the difference×the first average value)/(the second average value).

11. A non-transitory computer readable medium having instructions stored thereon for detecting a biomarker indicating a critical state before transitioning to a disease state of a target biological system based on data acquired by measuring the target biological system, the instructions causing a computing device to perform:
acquiring first correlation coefficients between a plurality of factor items in a reference dataset that is based on data acquire from a plurality of reference biological systems;
acquiring second correlation coefficients between a plurality of factor items in a target dataset that is adding, to the reference dataset, target biological data acquired from the target biological system;
acquiring difference correlation coefficients that are differences between the first correlation coefficients and the second correlation coefficients;
acquiring a first average value of the difference correlation coefficients between one factor item in the target biological data and a first one or more factor items having a prescribed correlation coefficient with respect to the one factor item, among the plurality of factor items;
acquiring an average value of a plurality of data items for the one factor item among the plurality of factor items in the reference dataset;
acquiring a difference between the average value and data of the one factor item in the target biological data;
acquiring each of indexes based on the difference and the first average value; and
detecting a factor item corresponding to the indexes as a new biomarker indicating the critical state before transitioning to the disease state of the target biological system.

12. A non-transitory computer readable medium having instructions according to claim 11, the instructions causing a computing device to perform:
acquiring a second average value of the difference correlation coefficients between the first one or more factor item and a second one or more factor items having a prescribed correlation coefficient with respect to the first one or more factor items, among the plurality of factor items, wherein the second one or more factor items does not comprise the one factor item; and
acquiring each of indexes by an equation given by (the difference×the first average value)/(the second average value).

* * * * *